(12) United States Patent
Bagga et al.

(10) Patent No.: US 6,676,662 B1
(45) Date of Patent: Jan. 13, 2004

(54) BONE INSTRUMENTS AND METHODS

(75) Inventors: Charanpreet S. Bagga, Phoenixville, PA (US); David A. Hanson, Minneapolis, MN (US); Dale L. Brady, Richfield, MN (US)

(73) Assignee: Sulzer Spine-Tech Inc., Minneapolis, MN (US)

( * ) Notice: Subject to any disclaimer, the term of this patent is extended or adjusted under 35 U.S.C. 154(b) by 254 days.

(21) Appl. No.: 09/692,512

(22) Filed: Oct. 19, 2000

Related U.S. Application Data

(60) Provisional application No. 60/160,484, filed on Oct. 20, 1999, and provisional application No. 60/197,040, filed on Apr. 14, 2000.

(51) Int. Cl.$^7$ .................................................. A61F 5/00
(52) U.S. Cl. ......................................................... 606/87
(58) Field of Search .............................. 606/87, 88, 89, 606/86, 96, 102, 54, 79

(56) References Cited

U.S. PATENT DOCUMENTS

| | | | | | |
|---|---|---|---|---|---|
| 5,053,039 | A | * | 10/1991 | Hofmann et al. | 606/87 |
| 5,364,401 | A | * | 11/1994 | Ferrante et al. | 606/84 |
| 5,601,563 | A | * | 2/1997 | Burke et al. | 606/86 |
| 6,030,391 | A | * | 2/2000 | Brainard et al. | 606/87 |
| 6,056,754 | A | * | 5/2000 | Haines et al. | 606/80 |

\* cited by examiner

*Primary Examiner*—Kevin Shaver
*Assistant Examiner*—Melba Bumgarner
(74) *Attorney, Agent, or Firm*—Merchant & Gould PC

(57) ABSTRACT

Bone guides for sizing or shaping bone are disclosed. The guides can be configured and sized for placement on a surgery table, instrument table or similar structure in an operating room. The guides provide for real time preparation of a bone graft during a surgical procedure.

8 Claims, 18 Drawing Sheets

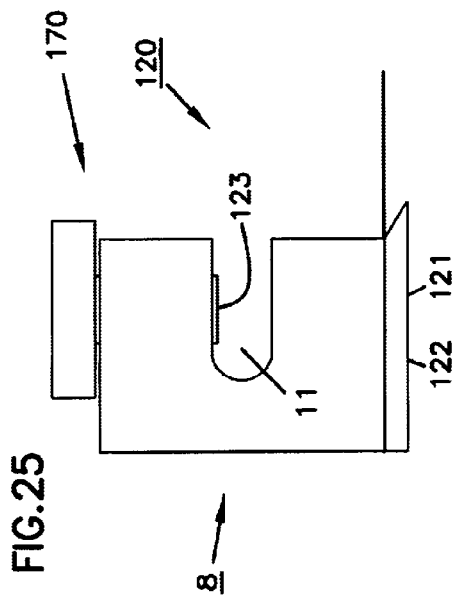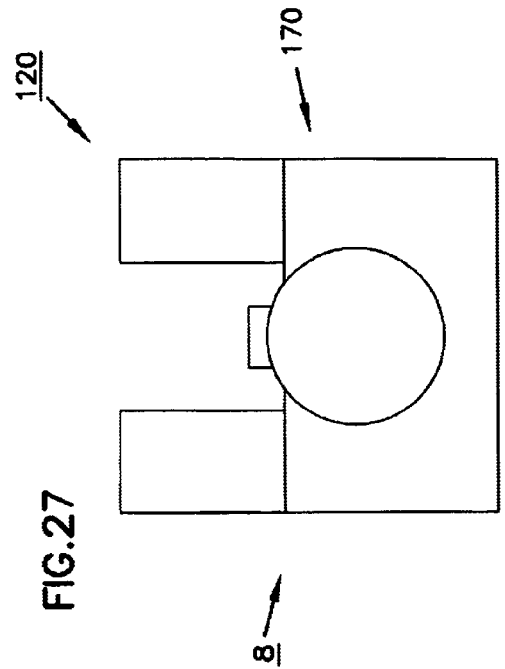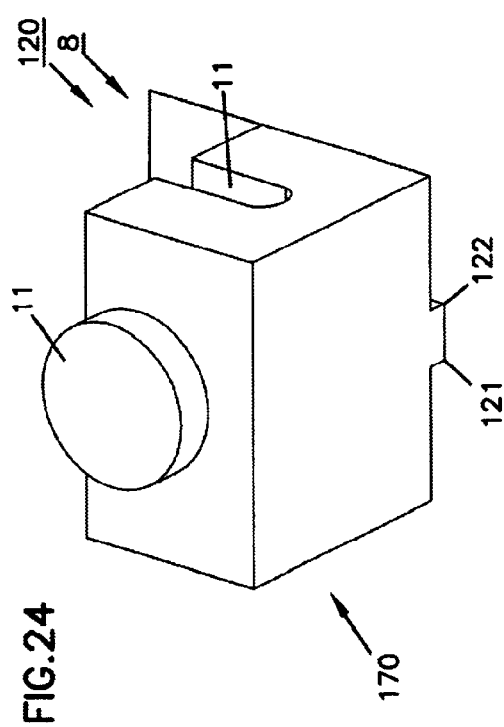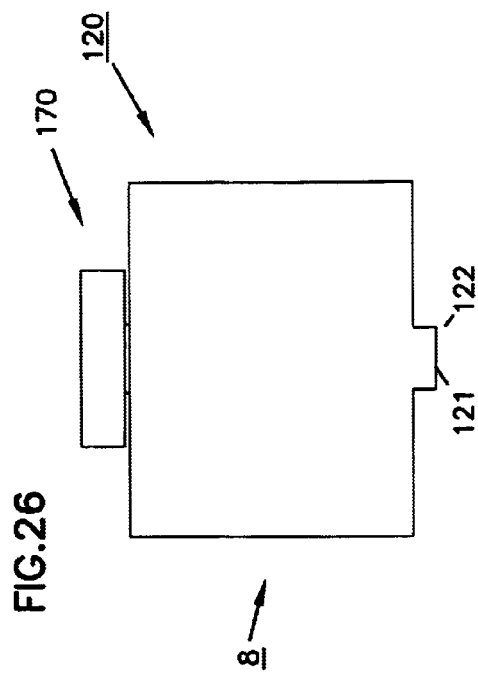

BONE INSTRUMENTS AND METHODS

RELATED APPLICATIONS

The present application claims priority to U.S. applications 60/160,484 filed Oct. 20, 1999, and 60/197,040 filed Apr. 14, 2000, the entire disclosures of each application being incorporated herein by reference.

FIELD OF THE INVENTION

The present invention is directed to the field of surgery. Specifically, the invention is directed to instruments and methods for cutting and shaping bone. The invention is particularly advantageous for cutting and shaping bone for use in bone grafting.

BACKGROUND OF THE INVENTION

Bone grafts are used in many types of bone surgery. Often times, bone used as a bone graft has been prepared according to generic size and shape specifications. However, preparing a bone graft during surgery can provide precisely configured bone at significantly reduced costs. Having instruments for sizing or shaping bone in the operating room can enhance the overall success of the surgical procedure by enabling the surgeon to fine tune the configuration of the graft for a particular site.

Accordingly, there is a need for instruments and methods to size and shape bone for a particular application. The present invention is directed to this need.

SUMMARY OF THE INVENTION

The present invention is directed to guides and methods for cutting or shaping bone. A guide (or jig) provides for maintaining a selected positional relationship between herein disclosed cutting or shaping instruments and bone that can be held by the jig. The guide can be configured and sized for placement on a surgery table, instrument table or similar structure for use in an operating room. In preferred embodiments, the jig is portable and manufactured from a material such as stainless steel (or other materials suitable for surgical use) which permits sanitization or sterilization using known procedures. The jigs provide real time preparation of a bone graft from heterologous, homologous, or autologous sources (i.e., xenograph, allograft, autograft).

Throughout the specification, guidance may be provided through lists of examples. In each instance, the recited list serves only as a representative group. It is not meant, however, that the list is exclusive.

Unlike many prior systems, the invention provides the surgeon with the flexibility to cut and shape a bone graft to any size or shape needed at the time of surgery. In some embodiments, the guides disclosed include a surface for cooperative fit with an inanimate object in the operating room. If necessary, the guides can be stabilized during use by one or more c-clamps or a similar fixating device or by a surgical assistant or other person holding the guide in a stable position during graft preparation.

The guides of the invention are suitable for use with any type of bone that is used for grafting in any location. In some embodiments, the guides are particularly advantageous for use in spinal surgery applications. Examples of bones which can be used for spinal applications include, without limitation, femur, tibia, patella and fibula. In the case of vertebral fusion procedures (e.g., intradiscal graft implant), femoral and tibial bone can typically be used as grafts for fusion of lumbar and thoracic vertebrae and fibular bone for cervical vertebrae.

In one embodiment, a guide according to the invention can include a base, bone holding arrangement, bone cutting arrangement having at least one cutting guide and a bone shaping arrangement. The bone holding arrangement can include a first and second bone holding member. A bone holding member typically includes a gripping end for contacting the bone. The gripping end can have any of various surface contours to facilitate secure engagement of the bone.

In an alternative embodiment, the bone cutting guide can include a base, a bone holding arrangement and a bone cutting arrangement including a first cutting block and a second cutting block. Each of the first and second cutting blocks can include a slot for passing a saw blade therethrough for cutting bone.

In another embodiment, a guide according to the invention can include a base, a bone holding arrangement and a bone cutting arrangement wherein the bone cutting arrangement includes at least one cutting guide. The cutting guide can include a slot for passing a saw therethrough and is arranged such that when bone is fixed in a first position by the bone holding arrangement, a saw passed through the slot in the first cutting guide can make a first cut in the bone at a first location. The cutting guide can then be repositioned and a second cut made with the saw at a second location in the bone.

The invention also provides methods for bone cutting and shaping.

BRIEF DESCRIPTION OF THE DRAWINGS

FIG. 24 is a perspective view of an alternative embodiment of a shaping block according to the invention;

FIG. 25 is a side view of the shaping block of FIG. 24;

FIG. 26 is a back view of the shaping block of FIG. 24;

FIG. 27 is a top view of the shaping block of FIG. 24;

DETAILED DESCRIPTION OF THE ILLUSTRATED EMBODIMENTS

The bone guides of the invention will be described by reference to the several drawing figures. The illustrated embodiments are provided only for descriptive purposes and are not intended to limit the guides that are within the scope of the invention.

In general, a guide of the invention functions to hold a bone or section of bone in a fixed position during cutting, shaping or other preparational procedure performed on the bone. Advantageously, in some embodiments, the guides disclosed herein provide a stereotaxic approach for precision sizing and shaping of bone for use in bone grafting.

Figure 1:
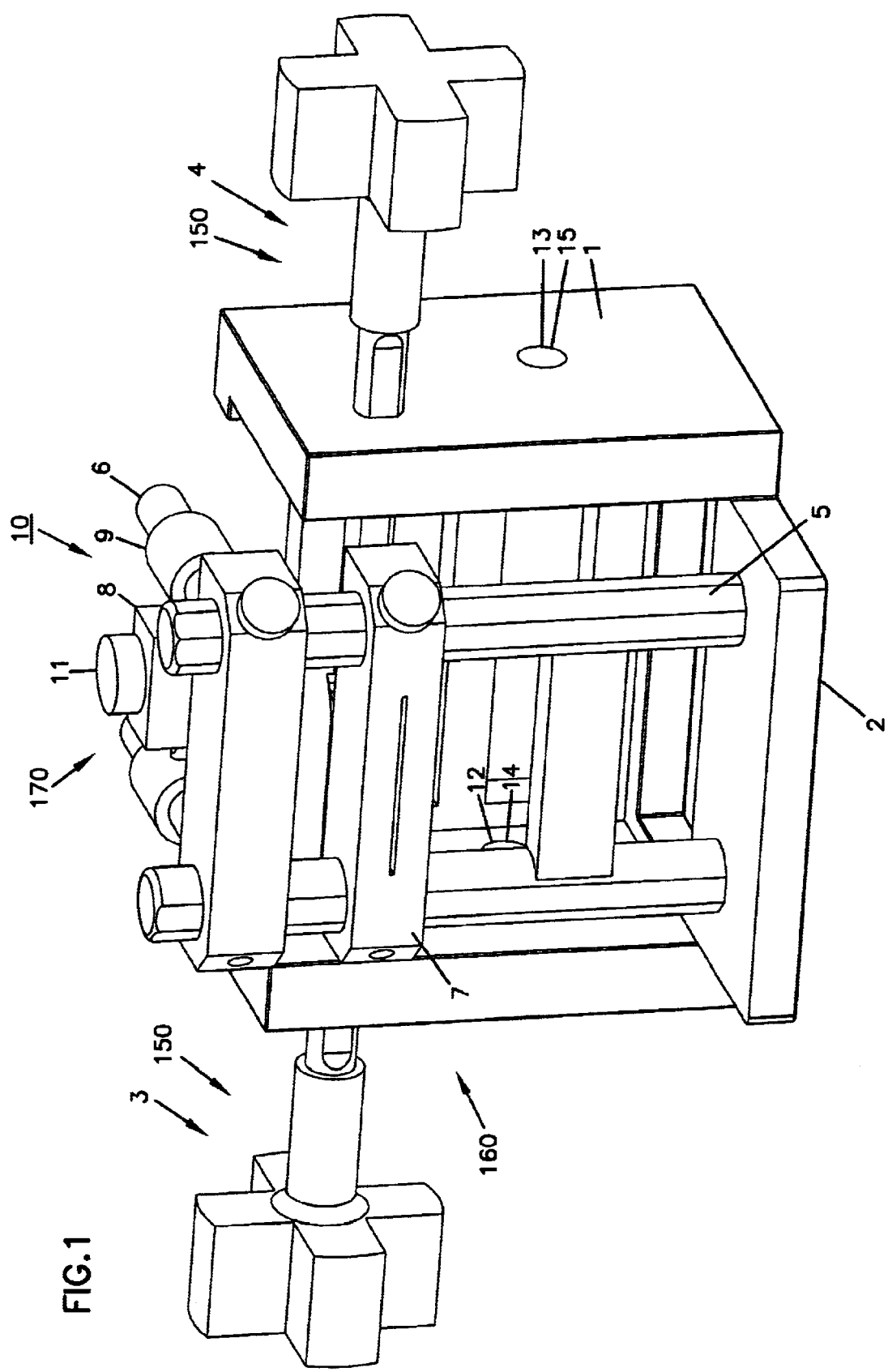
FIG. 1 is a side perspective view of one embodiment of a bone guide according to the invention.
Figure 2:
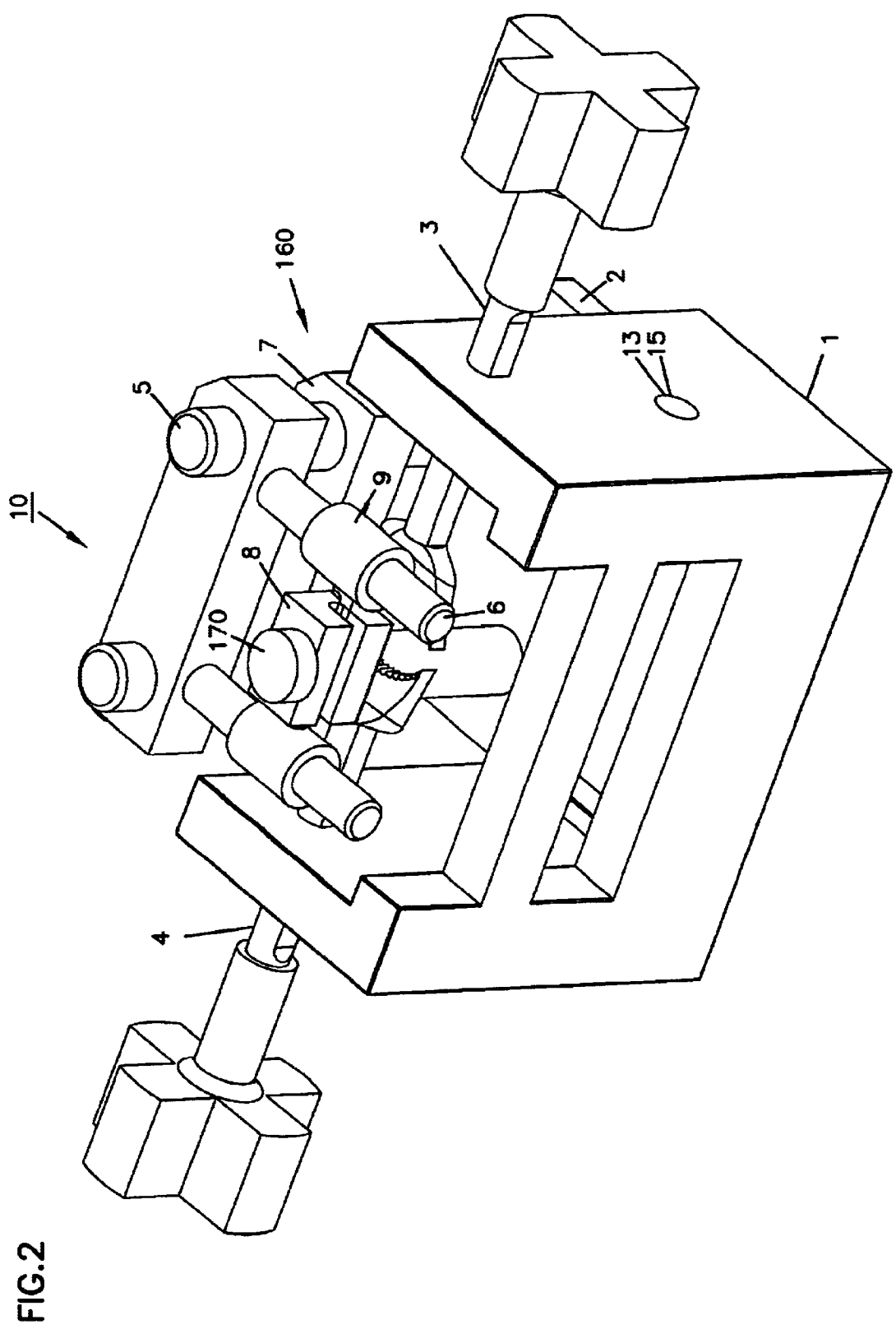
FIG. 2 is a top perspective view of the bone guide of FIG. 1.

FIG. 1 is a side perspective view and FIG. 2 a top perspective view of one embodiment of a guide 10 according to the invention. In this embodiment, guide 10 includes a body 1, a base 2 and a bone holding arrangement 150 including a first bone holding member 3 and a second bone holding member 4 which pass through body 1. Bone holding members 3 and 4 do not need to pass through body 1 to provide their herein disclosed functions.

A bone cutting arrangement 160 including a vertical track 5 mounted to body 1 and a cutting guide such as cutting block 7 is illustrated. Horizontal track 6 can be mounted to vertical track 5. However, it will be appreciated that horizontal track 6 could alternatively be mounted to body 1. Moreover, while referred to as vertical and horizontal tracks, it will be appreciated that the tracks of a jig of the invention need not be limited to vertical or horizontal. Rather, the horizontal and vertical tracks are used for explanatory purposes of the illustrated embodiment. Tracks configured at various degrees of angulation from vertical and horizontal are within the scope of the invention.

Figure 15:
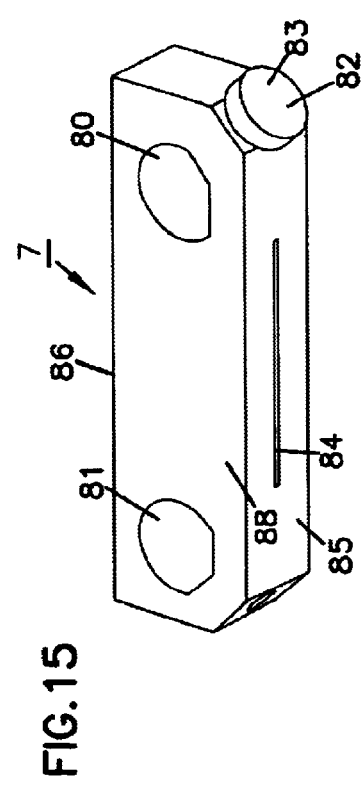
FIG. 15 is a perspective view of one embodiment of a cutting block.
Figure 17:
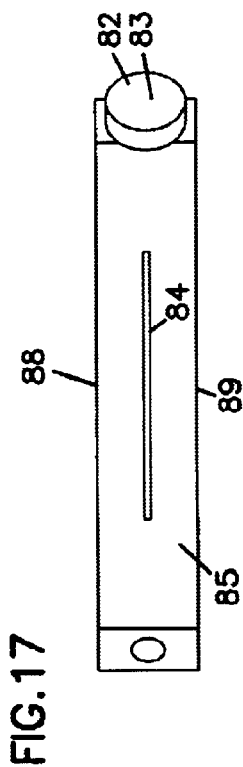
FIG. 17 is a front view of the cutting block of FIG. 15.
Figure 18:
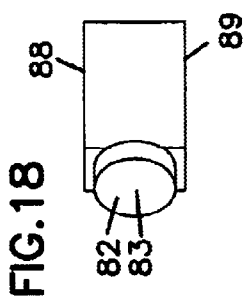
FIG. 18 is a side view of the cutting block of FIG. 15.
Figure 19:
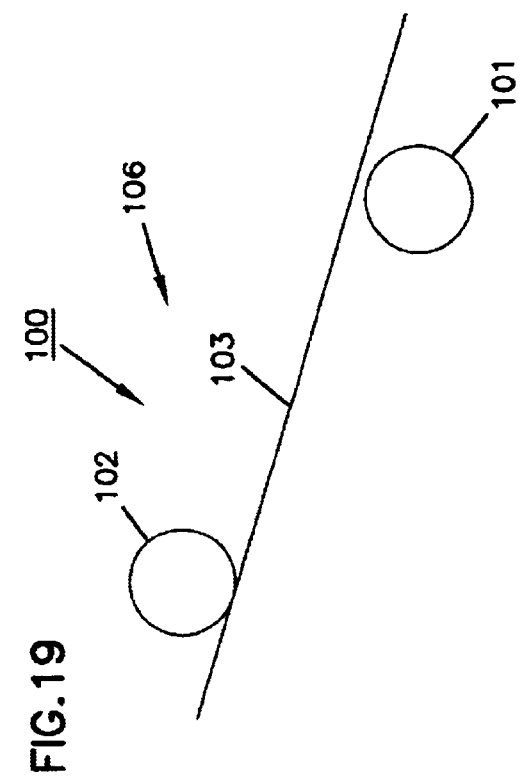
FIG. 19 is a diagrammatic representation of a side view of an alternative embodiment of a bone cutting arrangement of the invention.
Figure 22:
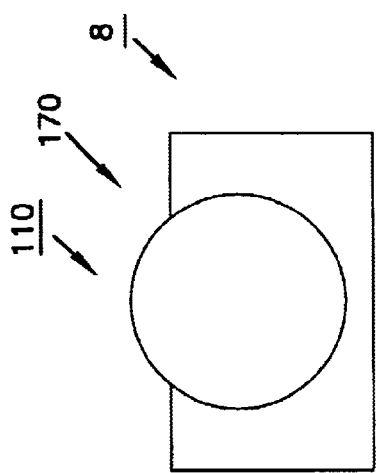
FIG. 22 is a top view of the shaping block of FIG. 20.
Figure 23:
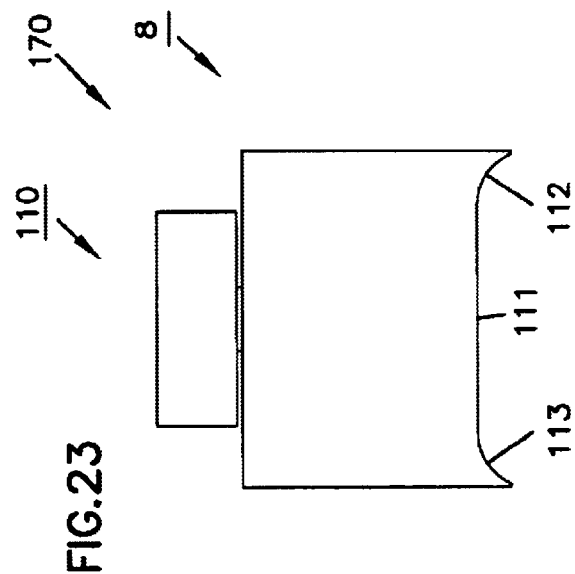
FIG. 23 is a back view of the shaping block of FIG. 20.
Figure 20:
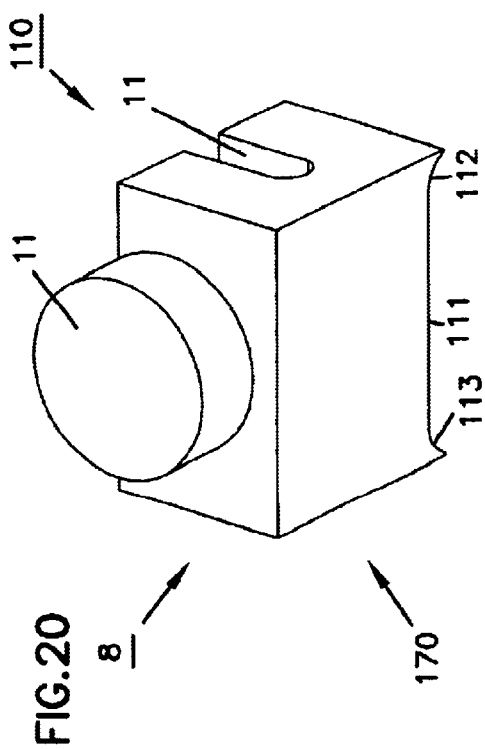
FIG. 20 is a perspective view of one embodiment of a shaping block according to the invention.
Figure 21:
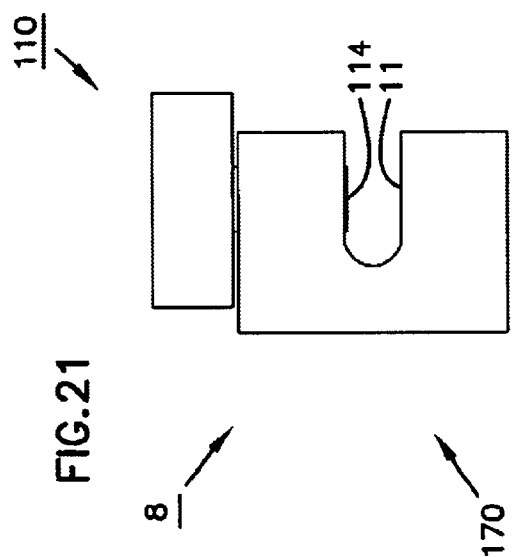
FIG. 21 is a side view of the shaping block of FIG. 20.
Figure 28:
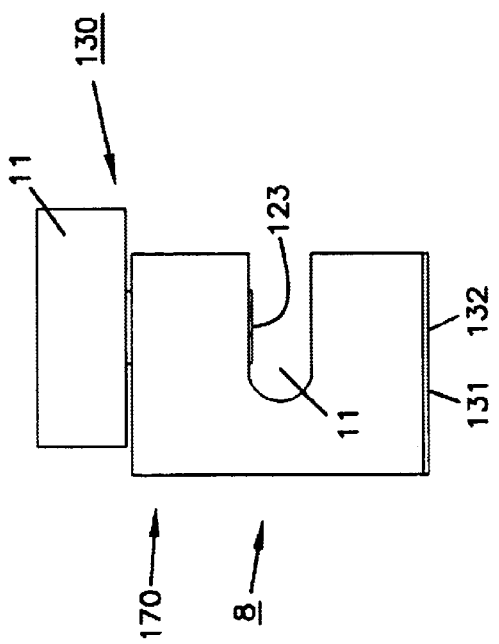
FIG. 28 is a perspective view of an alternative embodiment of a shaping block according to the invention.

Referring to FIGS. 1, 2 and 15, cutting block 7 can be mounted to vertical track 5 for vertical movement of cutting block 7 along the track, relative to first and second holding members 3, 4, respectively. It will be appreciated that cutting block 7 could alternatively be adjustably mounted directly to body 1.

Referring to FIGS. 1, 2, 11–14 and 20–31, one embodiment of a bone shaping arrangement 170 is illustrated. In this embodiment, bone shaping arrangement 170 includes a shaping block 8 mounted to shaping track 9 which is mounted to horizontal track 6. While the specific components of a bone shaping arrangement may vary, a bone shaping arrangement of the invention typically includes a cutting, grinding, rasping, or other surface to shape or provide a contour to a piece of bone. In the illustrated embodiment, shaping block 8 can be moved in a vertical direction along vertical track 5. In addition to vertical movement, shaping block 8 can also move in a first horizontal plane along shaping track 9 and in a second horizontal plane via horizontal track 6. Shaping block 8 can also include a portion of tracking mechanism 11 to maintain shaping block 8 in a selected orientation on shaping track 9 as will be discussed below.

Body 1 also includes a first stabilizing arrangement 12 and a second stabilizing arrangement 13 for fixing guide 10 in a particular location. For example, first and second stabilizing arrangements 12, 13 can be holes 14, 15, threaded or unthreaded, for mounting horizontally oriented handles (not shown). By exerting a downward force on such handles, guide 10 can be stabilized while in use. Alternatively, a c-clamp can be used to clamp base 2 to a stationary object, for example, a surgery table or instrument table. In another alternative, the jig may be used without the need for c-clamps or other ancillary stabilizing system.

Figure 4:
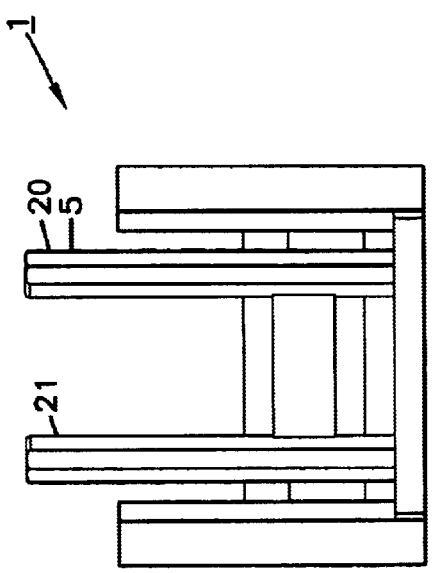
FIG. 4 is a front view of the body of FIG. 3.
Figure 6:
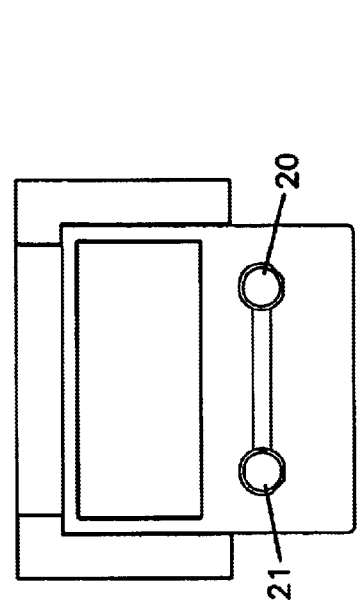
FIG. 6 is a top view of the body of FIG. 3.
Figure 3:
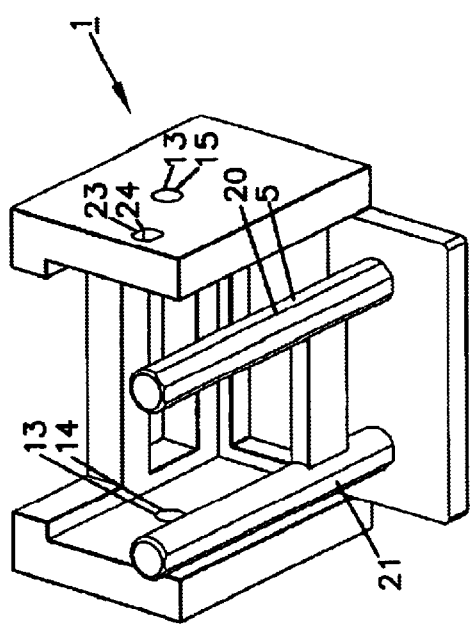
FIG. 3 is a top perspective view of an embodiment of a body of a jig of the invention.
Figure 5:
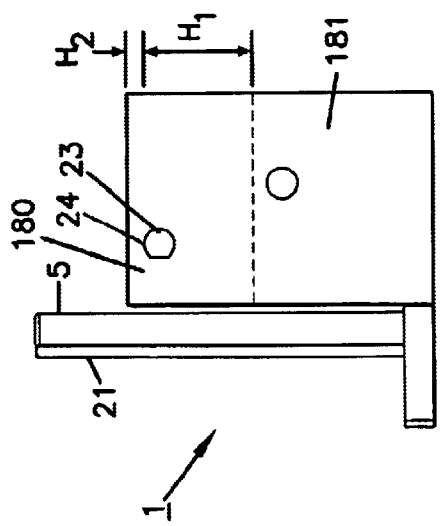
FIG. 5 is a side view of the body of FIG. 3.

FIGS. 3–6 illustrate an embodiment of body 1 of jig 10 with certain components removed for easier visualization. FIG. 3 is a top perspective view, FIG. 4 is a front view, FIG. 5 is a side view and FIG. 6 is a top view. In the illustrated embodiment, vertical track 5 comprises a first vertical member 20 and a second vertical member 21. However, in some embodiments, vertical track 5 may have only a single track member. Whether a single track member or multiple track members, in some embodiments, vertical track 5 can also include a rack which meshes with a pinion located, for example, on cutting block 7, for incremental movement of cutting block 7 along vertical track 5. Vertical track 5 can also include graduated markings to indicate relative positions of cutting block 7 along vertical track 5. Body 1 can also include a rotation limiter 23 such as first holder opening 24 and second holder opening (not visible) through which holding members 3 and 4 are passed. The bone holder openings can be configured, such as having a "D" shape, to limit rotational movement of the bone holding members.

Figure 7:
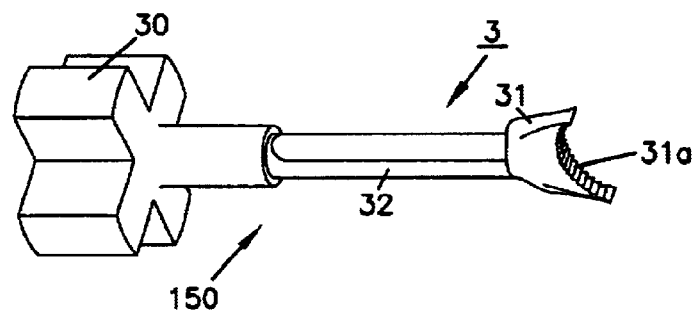
FIG. 7 is a perspective view of one embodiment of a bone holding member.
Figure 8:
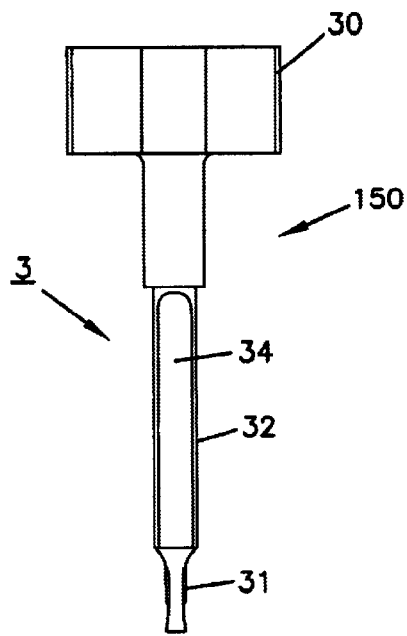
FIG. 8 is a top plan view of the bone holding member of FIG. 7.
Figure 9:
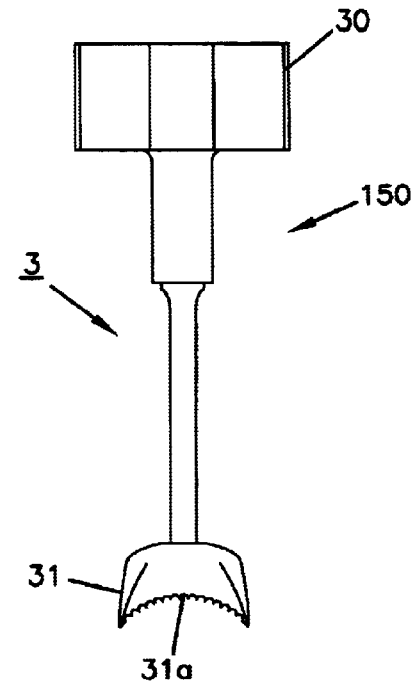
FIG. 9 is a view of the bone holding member of FIG. 8 rotated 90°.

FIG. 7 is a perspective view of one embodiment of a first bone holding member 3. The second bone holding member 4 may be identical in appearance. FIG. 8 is a top view of the bone holding member of FIG. 7 and FIG. 9 is a top view of the holding member of FIG. 8 rotated 90° about the longitudinal axis of bone holding member 3. As illustrated, bone holding member 3 includes an operating end 30 and a gripping end 31. Gripping end 31 directly contacts bone that is prepared in guide 10 and preferably includes an engaging surface 31a for frictional gripping of the bone. Suitable engaging surfaces are known and include, for example, serrations, grooves, ridges, knurls, etc. A shaft 32 extends between operating end 30 and gripping end 31. Shaft 32 is preferably configured to limit rotational movement of bone holding member 3 when within body 1. For example, in the illustrated embodiment, bone holding member 3 includes a groove 34 which can cooperate with a rotation limiter 23, such as a pin mounted onto body 1 (not illustrated) which maintains groove 34, and the entire bone holding member, in a fixed rotational position.

Figure 10:
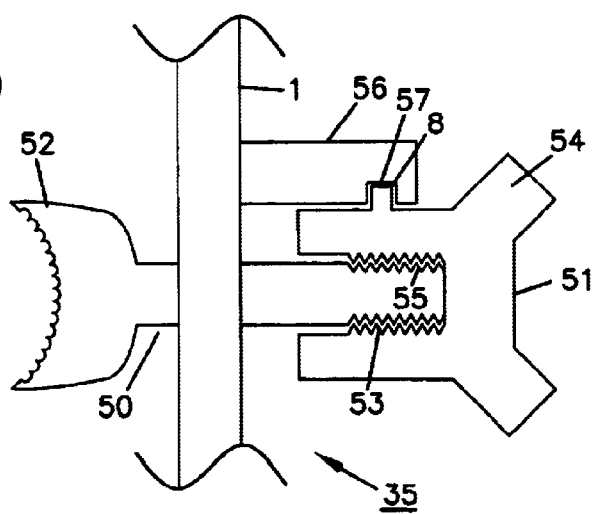
FIG. 10 is a view of an alternative embodiment of a bone holding member within a portion of the body of a jig according to the invention.

FIG. 10 is a top view of an alternative embodiment of a bone holding member 50 passing through body 1. According to this embodiment, bone holding member 50 includes an operating end 51 and a gripping end 52. Threads 53 of adjustment knob 54 at operating end 51 cooperate with threads 55 of bone holding member 50 when adjustment knob 54 is rotated. Rotation of adjustment knob 54 can advance or retract bone holding member 50 relative to an opposing bone holding member. Arm 56 is mounted to body 1 and includes a slot 57 that receives guide ring 58 of adjustment knob 54 to maintain adjustment knob 54 in position as holding member 50 is advanced or retracted.

Figure 11:
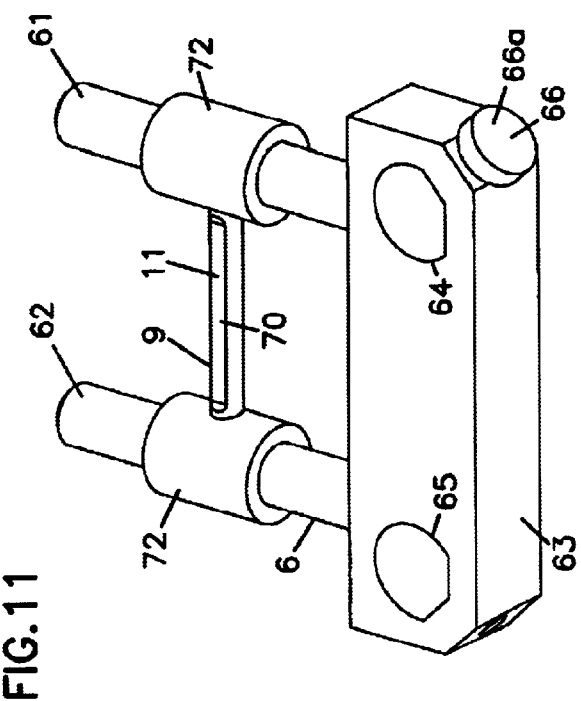
FIG. 11 is a perspective view of one embodiment of a horizontal track, carriage and shaping track.

Referring to FIG. 11, a perspective view of horizontal track 6 and shaping track 9 of a bone shaping arrangement is shown. In the illustrated embodiment, horizontal track 6 comprises a first horizontal member 61 and a second horizontal member 62 which extend from carriage 63. It will be appreciated that horizontal tracks could alternatively comprise only a single horizontal track member.

Carriage 63 includes a first opening 64 and a second opening 65 for passing along first vertical member 20 and second vertical member 21 of body 1. Carriage 63 also includes a releasable locking arrangement 66 (such as a threaded screw with knob 66a) for releasably locking carriage 63 at a selected position along the length of vertical track 5.

Figure 13:
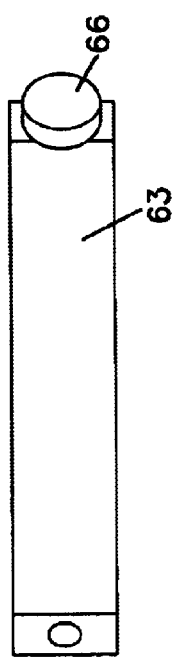
FIG. 13 is a front view of the carriage of FIG. 11.
Figure 14:
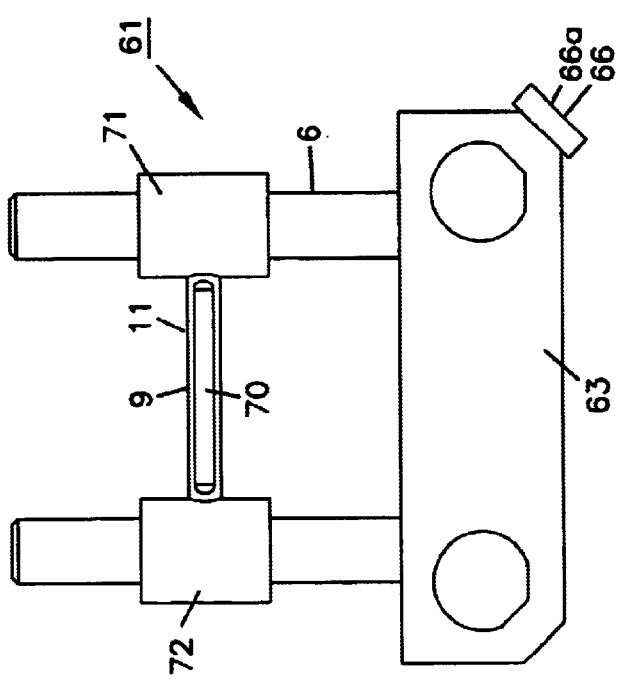
FIG. 14 is a top view of the horizontal track, carriage and shaping track of FIG. 11.
Figure 12:
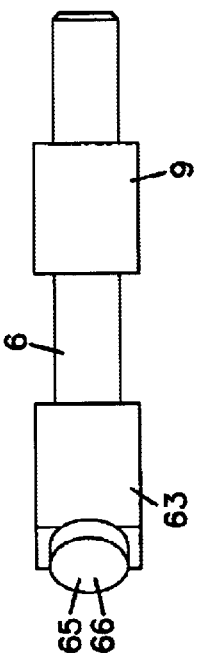
FIG. 12 is a side view of the horizontal track and carriage of FIG. 11.
Figure 16:
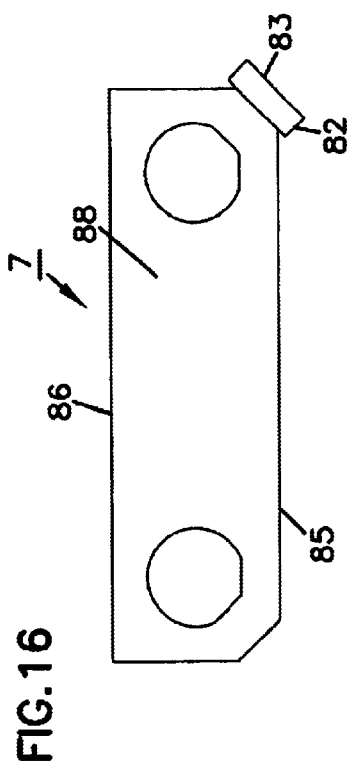
FIG. 16 is a top view of the cutting block of FIG. 15.

FIG. 12 is a side view of horizontal track 6 and carriage 63. FIG. 13 is a front view of carriage 63 and FIG. 14 is a top view of horizontal track 6, shaping track 9 and carriage 63. Referring to FIG. 14, shaping track 9 includes a first end including first tracking coupler 71 and a second end including a second tracking coupler 72. Thus, shaping track 9 can move back and forth along horizontal members 61, 62 in a plane horizontal to vertical track 5. As will be discussed below, shaping track 9 includes a portion of tracking mechanism 11, a shaping slot 70, for receiving a cooperating portion of tracking mechanism 11 on shaping block 8.

FIG. 15 is a perspective view of a cutting guide, cutting block 7, of a bone cutting arrangement. Cutting block 7 includes a first opening 80 and a second opening 81 for passage along first vertical member 20 and second vertical member 21. Cutting block 7 also includes a releasable locking arrangement 82 such as a threaded screw and knob 83 for locking cutting block 7 in a selected position along vertical track 5. Cutting block 7 also includes a cutting slot 84 for receiving the blade of a saw which can be passed through slot 84 from the front 85 of cutting block 7 through the back 86 to a position for cutting bone positioned between first and second holding members 3, 4. In the illustrated embodiment, slot 84 is parallel to the horizontal plane. However, cutting block 7 can include a slot which extends from front 85 to back 86 and which has an angle relative to horizontal of up to±90°, typically about 0° to 60°. Slot 84 maintains the saw blade (not shown) at the selected angle during cutting. It will be appreciated, however, that rather than passing through slot 84, a saw blade can be positioned against the top 88 or bottom 89 of cutting block 7 to maintain the position of the saw blade relative to a piece of bone. The positioning of the slot permits cutting bone such that the cut edges are parallel or angled relative to one another.

In an alternative embodiment, a saw blade can be maintained in a selected position using a bone cutting arrangement 160 such as saw stabilizing arrangement 100. According to this embodiment, a first saw guide member 101 is positioned a selected distance above or below a second saw guide member 102 such that when a saw blade 103 is passed between first saw guide member 101 and second saw guide member 102, the saw blade 103 is maintained at the selected angle for cutting a piece of bone. The saw guide members 101, 102 can be selectively positioned, for example, along vertical track 5 and spaced apart the appropriate distance between the first and second saw guides 101, 102 to form a desired angle using known releasable locking arrangements.

FIGS. 20–23, 24–27 and 28–30 are each alternative embodiments of a shaping block 8 according to the invention. Referring to FIGS. 20–23, rounding block 110 can round an outer surface of bone and includes a cutting surface 111 having a first curved side 112 and a second curved side 113. When rounding block 110 is in position on shaping track 9, and pin 114 of tracking mechanism 11 is positioned in shaping slot 70 (FIG. 11), rounding block 110 can be moved back and forth over a piece of bone in at least two horizontal directions, one along horizontal track 6 and the second along shaping track 9.

FIGS. 24–27 illustrate an alternative embodiment of a shaping block 8. According to this embodiment, ribbed block 120 includes a cutting surface 121 having a ridge 122 which can create a groove in a bone when passed back and forth over the bone. FIG. 25 is a side view of ribbed block 120, FIG. 26 is a back view of ribbed block 120 and FIG. 27 is a top view of ribbed block 120. Ribbed block 120 also includes a pin 123 of tracking mechanism 11 as described above for rounding block 110.

Figure 29:
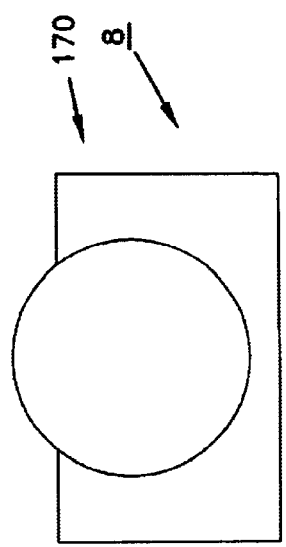
FIG. 29 is a side view of the shaping block of FIG. 28.
Figure 30:
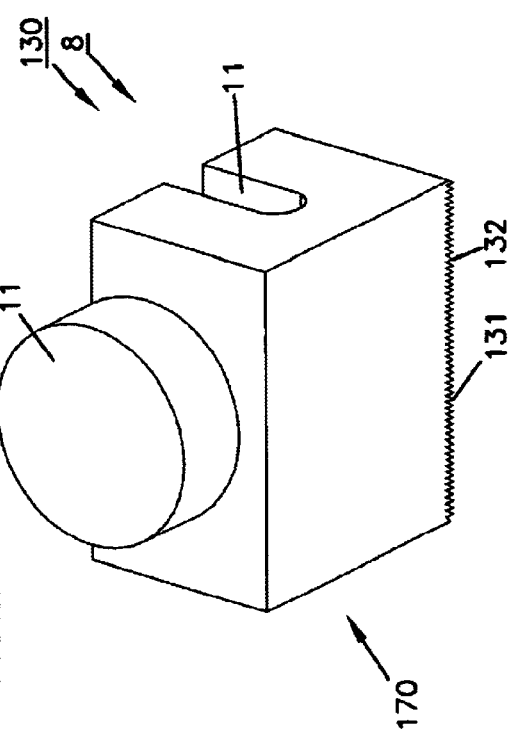
FIG. 30 is a back view of the shaping block of FIG. 28.
Figure 31:
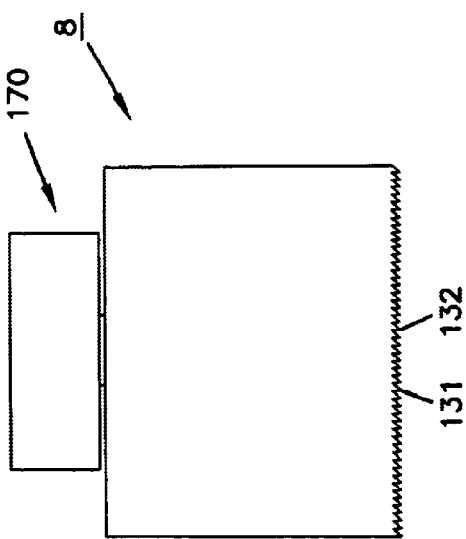
FIG. 31 is a top view of the shaping block of FIG. 28.

FIGS. 28–31 illustrate another embodiment of a shaping block 8. According to this embodiment, serrated block 130 includes a cutting surface 131 having serrations 132 which can shave bone when passed back and forth over the bone. FIG. 29 is a side view of serrated block 130, FIG. 30 is a back view of serrated block 130 and FIG. 31 is a top view of serrated block 130. Serrated block 130 also includes a pin 133 of tracking mechanism 11 as discussed above for rounding block 110.

During use of guide 10, a surgeon can determine an initial size and shape of bone to be used, for example, for a bone graft, in vivo or using x-rays, MRI, CT-scans, etc. Once the bone source is selected, it can be placed within the bone holding arrangement, such as between the gripping ends of a pair of bone holding members and the members are advanced towards one another to secure the bone in place.

An appropriate bone cutting arrangement, such as a cutting block, saw stabilizing arrangement, etc., and bone shaping arrangement are selected. The cutting block can be mounted to the jig and a saw such as an oscillating saw, can then be used to make a first cut of bone. The cutting block can then be repositioned if a second cut is needed to obtain a desired width dimension of the bone. If a different cutting block providing a different slot angle is desired, it can also be put onto the vertical track before making the second cut. The first or second cut can be made to achieve a flat or lordotic (angled) piece of bone of a desired width.

For shaping, the bone can be repositioned in the gripping end of the bone holding members. A bone shaping block can then be mounted onto the horizontal track at a selected position. The shaping block can then be passed back and forth over the bone, each pass removing an incremental amount of bone until the desired shape is cut into the piece of bone. Different shaping blocks can be used as necessary.

In an alternative embodiment, body 1 can be modular. Referring to FIG. 5 for description purposes, according to this alternative, body 1 could include a removable upper portion 180 separable from a lower portion 181 at a distance below rotational limiter 23. This configuration provides a height dimension $H_1$ below the rotational limiter that is greater (as illustrated) or less than the distance $H_2$ between rotational limiter 23 and the top edge of the upper portion. Thus after making a first cut through the bone with the removable upper portion oriented as in FIG. 5, the removable portion 180 (including the bone holding member and bone) can be rotated 180° and reset on the lower portion 181 of the body 1. The bone is then in a new position for making the second cut with the cutting block position unchanged.

The base of the jig can include one or more legs, typically four, which rest on a stationary object. The legs can be telescoping or modular for increasing or decreasing the height of the jig relative to the table as desired.

Figure 32:
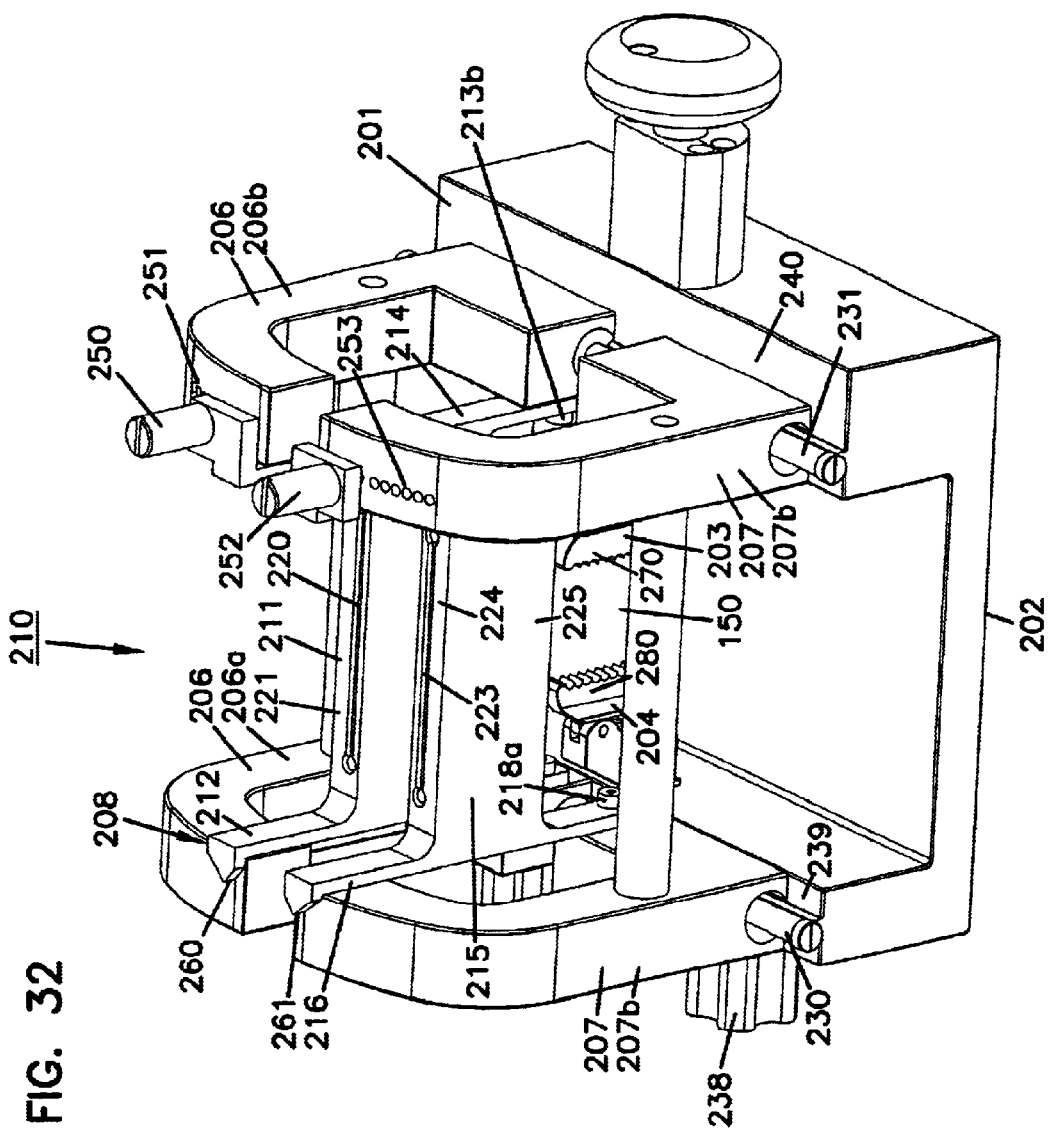
FIG. 32 is a perspective view of one embodiment of a bone guide according to the invention.
Figure 33:
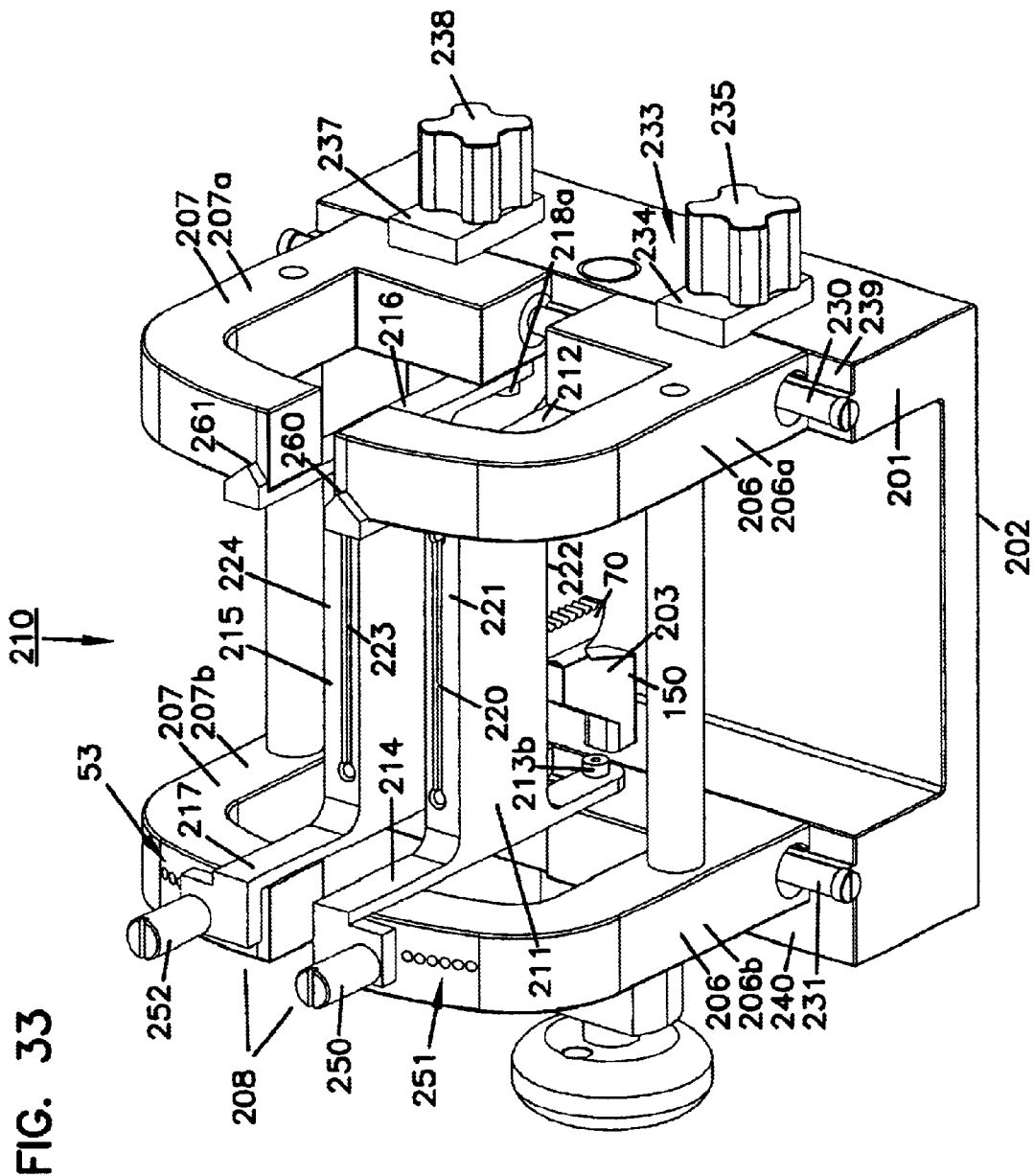
FIG. 33 is a perspective view of the bone guide of FIG. 32 rotated 180°.
Figure 34:
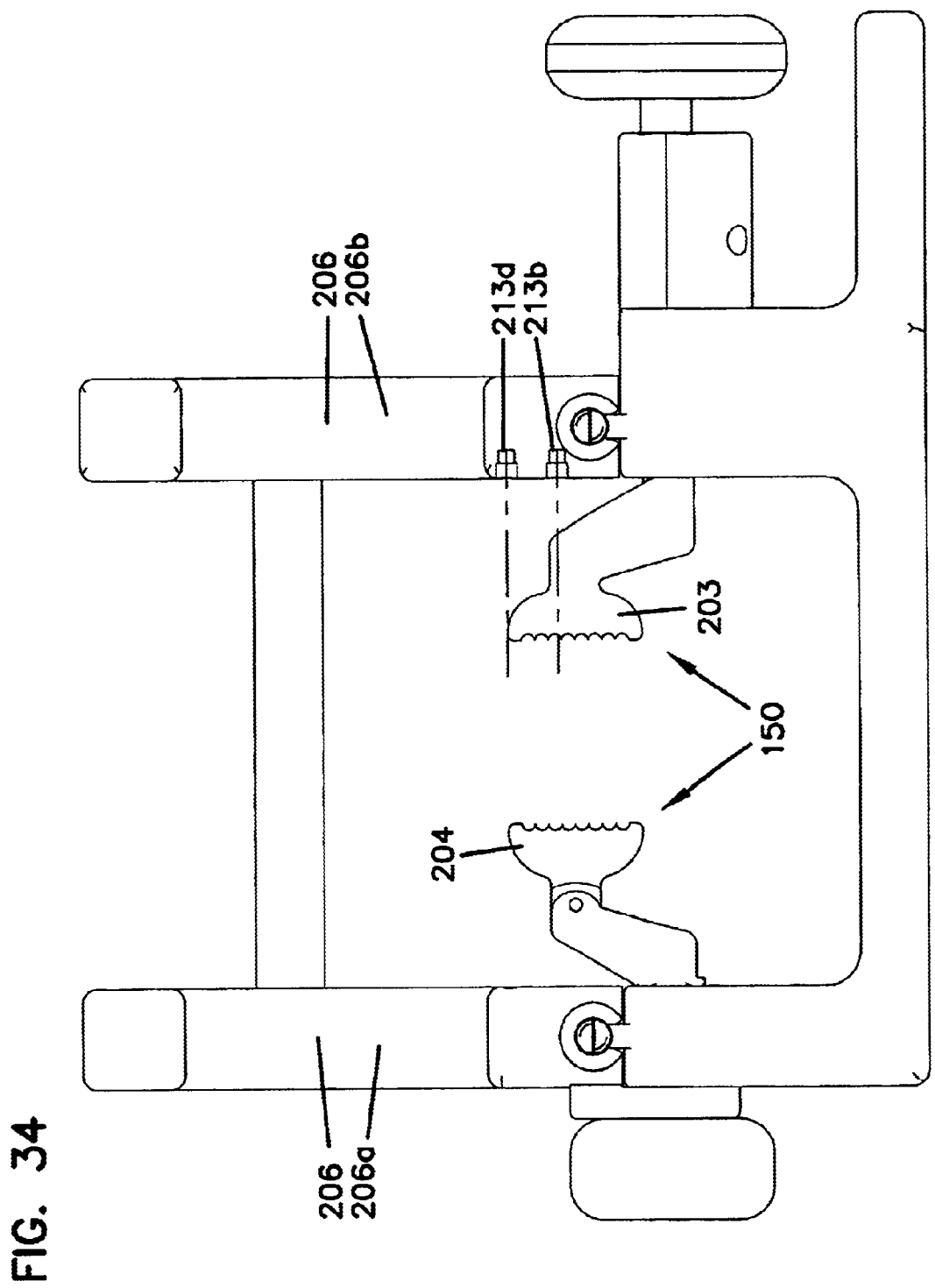
FIG. 34 is a front end view of a portion of the bone guide shown in FIG. 32.

FIGS. 32 to 34 illustrate an alternative embodiment of a bone guide 210 according to the invention. FIG. 32 is a perspective view of bone guide 210. FIG. 33 is a perspective view of the bone guide 210 of FIG. 32 rotated 180°. Bone guide 210 includes a body 201, a base 202, a bone holding arrangement 150 comprising first bone holding member 203 and a second bone holding member 204. A first support member 206 has a first pair of support arms 206a, 206b and a second support member 207 has a second pair of support arms 207a, 207b. The first support member 206 and second support member 207 can be opposed to each other and in slidable relationship relative to one another and to body 201.

A bone cutting arrangement 208, comprising a bone cutting guide such as first cutting block 211 mounted to a first pivot arm 212 and a second pivot arm 214 which can rotate around pivot points 213a (not visible) and 213b of first support member 206. Second cutting block 215 can be mounted to a third pivot arm 216 and a fourth pivot arm 217 which can rotate around pivot points 218a, 218b (not visible) of second support member 207. Thus, first cutting block 211 can be pivoted on first pivot arm 212 and second pivot arm 214 relative to first support member 206 and second cutting block 215. Second cutting block 215, in combination with third pivot arm 216, fourth pivot arm 217 and pivot points 218a and 218b, have a similar relationship to second support member 207 and first cutting block 211.

FIG. 34 is a front view of bone guide 210 as shown in FIG. 32. Portions of bone cutting arrangement 208 have been removed to visualize pivot point 213a. As illustrated in FIGS. 32 and 33, pivot point 213a and 213b (and 218a and 218b) can be located along an axis that passes through bone holding members 203 and 204. However, in alternative embodiments, pivot points such as illustrated pivot point 213d (213c on the opposite side not shown for this description) can be located above the bone holding members 203 and 204.

Referring again to FIGS. 32 and 33, first cutting block 211 includes a first cutting slot 220 extending from proximal edge 221 to distal edge 222. Second cutting block 215 includes a second cutting slot 223 extending from proximal edge 224 to distal edge 225 of cutting block 215.

The foregoing components are arranged such that when a piece of bone is secured within the bone holding arrangement 150, such as between first bone holding member 203 and second bone holding member 204, a bone saw, such as an oscillating bone saw, can be passed into first cutting slot 220 to make a first cut into the bone and subsequently into second cutting slot 223 to make a second cut into the bone.

The relative position of first cutting block 211 to second cutting block 215 determines the spacing between cuts made into the bone. In one embodiment, when first cutting block 211 is in direct contact with second cutting block 215, the spacing between first cutting slot 220 and second cutting slot 223 is approximately 6 mm. This also being the approximate thickness of a section of bone that can be cut when the first and second cutting blocks are in this position. Thus, the position of first cutting block 211 and second cutting block 215 during cutting can determine whether the cut edges of the bone are parallel or angled relative to one another.

In another embodiment, it will be appreciated that only a single cut may be necessary to provide a piece of bone having a particular thickness. For example, referring to FIG. 32, an affirmative stop (not shown), such as a flat sheet of stainless steel, can be inserted into first cutting slot 220 extending from proximal edge 221, beyond distal edge 222 and distally beyond bone holding arrangement 150 to contact the top surface of base 202. A length of bone can then be inserted into bone holding arrangement 150 with one end of the bone abutting against the affirmative stop. Second cutting block 215 can then be positioned at a selected distance from first cutting block 211 and a saw passed into second cutting slot 223 and the bone cut. Thus, according to this example, the end of the bone abutting against the affirmative stop is not cut at this time.

In the illustrated embodiment, first support member 206 and second support member 207 can be selectively moved relative to one another by sliding back and forth along first linear track guide 230 and second linear track guide 231. Referring to FIG. 33 when first support member 206 is positioned at a selected location it can be fixed into position by a first locking arrangement 233. In the illustrated embodiment, first locking arrangement 233 includes a first compression plate 234 which secures the first support member 206 in position when first securing knob 235 is rotated to threadedly compress compression plate 234 against first support member 206. A similar arrangement for locking second support member 207 includes a second locking arrangement 236 comprising second compression plate 237 and second securing knob 238.

Figure 35:
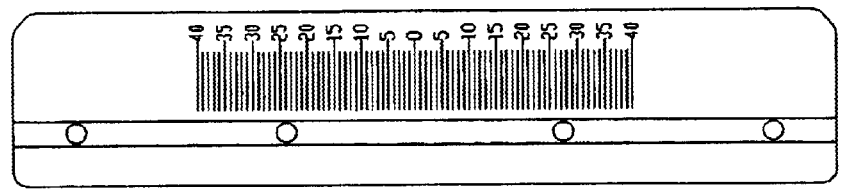
FIG. 35 is an example of graduated markings for use according to the invention.

In an alternative embodiment, body 201 can include a rack, for example along each of edges 239 and 240, which meshes with a pinion located on each of support members 206 and 207, for incremental movement of support member 206 and support member 207 relative to one another. The rack could alternatively be located on the support arms 206, 207 and the pinion on body 201. An indicator including markings such as shown in FIG. 35 can be mounted along edge 239 or 240 for measuring the distance between support arms 206 and 207.

Referring again to FIGS. 32 and 33, in this embodiment, pivot arms 212 and 214 can be secured in a selected position by threading first set screw 250 into a selected one of receptacles 251 located along first support member 206. Likewise, pivot arms 216 and 217 can be secured in a selected position by threading second set screw 252 into a selected one of receptacles 253 mounted along second support member 207. Securing pivot arms at a selected location can alternatively be accomplished using other arrangements known in the art including, for example, compression securing arrangements, etc., or, a rack and pinion system for incrementally adjusting the relative position of the pivot arm pairs relative to one another.

Figure 36:
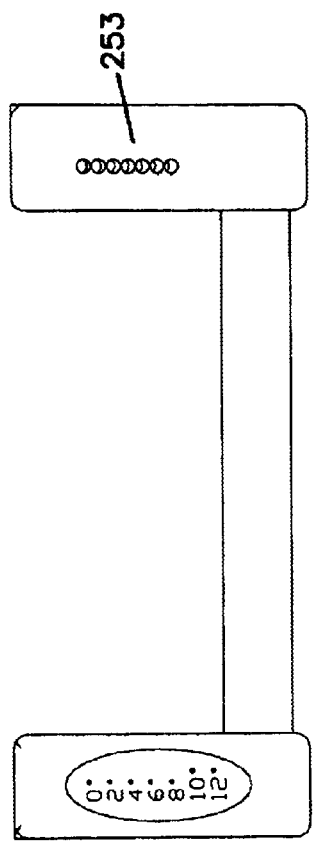
FIG. 36 is an example of graduated markings for use according to the invention.

An indicator arrangement such as apexes 260 and 261, located on pivot arms 212 and 214, respectively, can be present to assist the surgeon in confirming the spacing between cutting blocks. That is, apices 260 and 261 can be used in conjunction with graduated markings, for example as shown in FIG. 36, to indicate the amount of spacing or angle between the cutting blocks or cutting slots. As stated earlier, markings to indicate the spacing between the cutting blocks could also be located, for example, on edges 239 or 240.

Figures 37, 38:
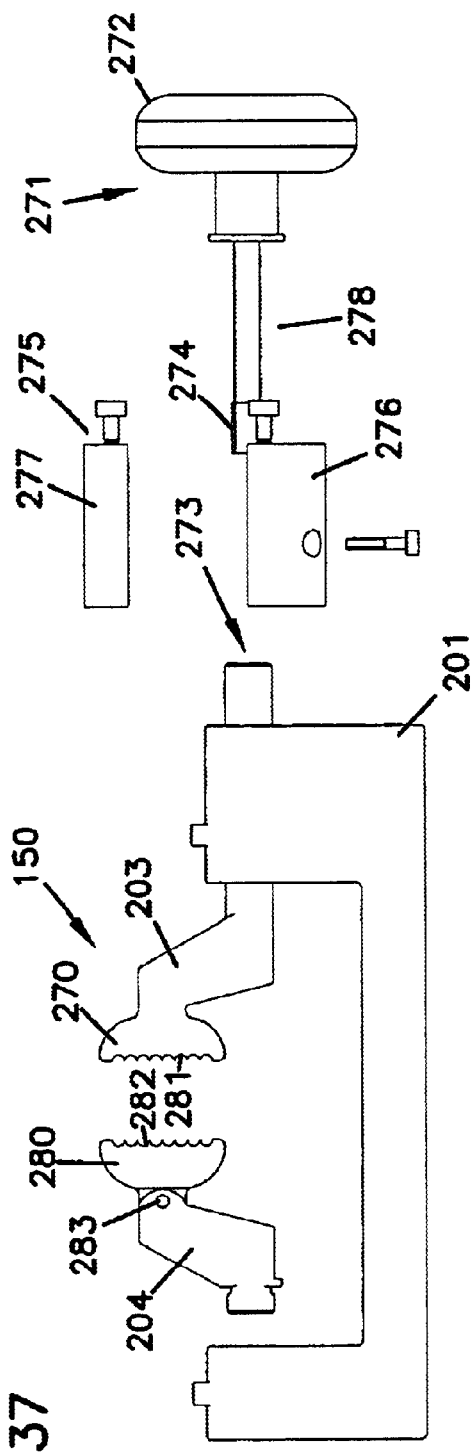
FIG. 37 is an end on view of bone holding members of one embodiment of a bone holding arrangement for a bone guide such as that of FIG. 32, and related components.
FIG. 38 is an alternative embodiment of engaging surfaces of a bone holding arrangement of the invention.

Referring now to FIG. 37, there is illustrated an end on view of a bone holding arrangement 150 (viewed from the end shown nearest the reader in FIG. 32) of bone holding members 203 and 204 relative to body 201 with omission of first and second support members and other components for easier viewing. First bone holding member 203 includes a gripping end 270 and an operating end 271 including a securing knob 272 for varying the position of bone holding member 203 relative to bone holding member 204. In the illustrated embodiment, bone holding member 203 includes a threaded bore 273 for receiving threaded shaft 274 which is attached to securing knob 272. Rotation of securing knob 272 rotates threaded shaft 274 within threaded bore 273 to move gripping end 270 to and fro relative to gripping member 204. Housing assembly 275 includes coaptating pieces 276 and 277 which function using known technology to cause gripping end 270 to move to and fro when securing knob 272 is rotated rather than permitting shaft 278 to move to and fro.

Bone holding member 204 also includes a gripping end 280. Opposite the gripping end 280, bone holding member 204 can be fixedly attached to body 201 or, alternatively, can include an operating end similar to that of bone holding member 203 for moving gripping end 280 to and fro relative to gripping end 270.

Gripping ends 270 and 280 directly contact bone that is to be prepared in guide 210 and preferably include an engaging surface 281 and 282, respectively, for engaging the bone. Suitable engaging surfaces are known and include, for example, serrations, grooves, ridges, knurls, or other textured surfaces.

In the illustrated embodiment, gripping end 270 is rigidly fixed to bone holding member 203 and gripping end 280 is pivotably mounted to bone holding member 204 via gripping pin 283. It will be appreciated that either or both of the gripping ends can be rigidly or pivotably mounted. In addition, the gripping ends or bone holding members can be modular for selective removal from guide 210 and interchangeability with any one of an array of different gripping ends or bone holding members for use as needed for a particular piece of bone.

As shown in FIG. 38, in one embodiment, engaging surfaces 270 and 280 can include engaging surfaces 281 and 282 configured for providing four-point contact with a piece of bone (B).

As described earlier, in use, a surgeon can determine an initial size of bone to be used for a bone graft in vivo or using x-rays, MRI, CT-scans, etc. Once a bone source is selected, it can be placed between the gripping ends of the bone holding members and one or both of the gripping members advanced towards one another to secure the bone in place. A saw can then be passed through, for example, first cutting slot 220 to make a first cut and through second cutting slot 223 to make a second cut. Alternatively, it is foreseen that the saw can be passed through cutting slot 220 (or 223) to make a first cut, and the bone then moved to a second location and a second cut made using the same slot as used for the first cut. In any embodiment, the first and/or second cut can be made to provide a cut surface of the bone that is in a plane which 0°–90° relative to a side surface of the bone. In fact, the guide provides for repositioning the bone in any orientation to make a cut on any surface and provide any dimension or degree of angulation.

Figure 39:
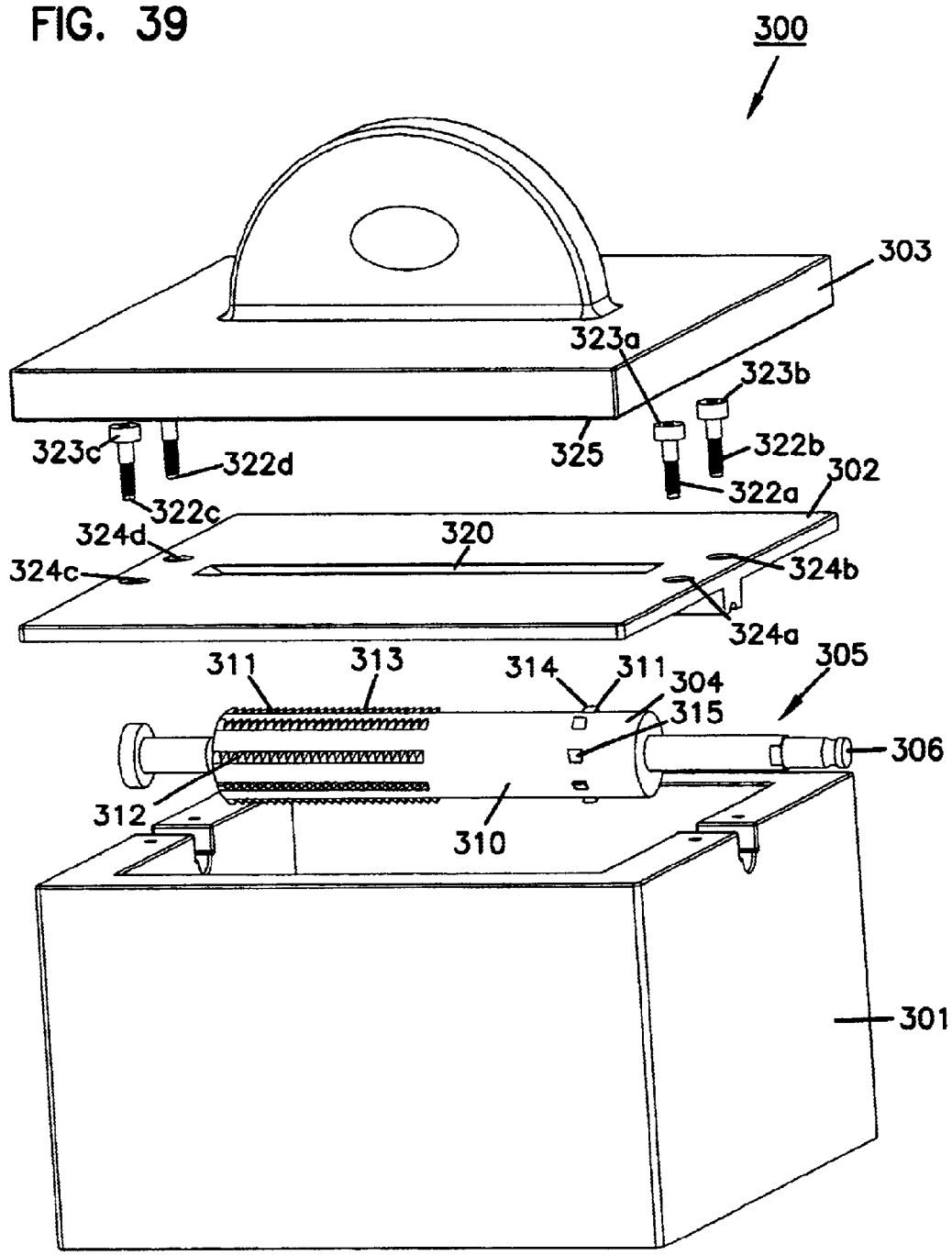
FIG. 39 is an exploded view of a shaping assembly according to the invention.

FIG. 39 illustrates an alternative embodiment of a bone shaping assembly 300 according to the invention. Shaping assembly 300 includes a frame 301, table surface 302 and cover guide 303. A shaping member 304 is rotatably mounted in frame 301. At a first end 305 shaping member 304 includes a coupler 306 for coupling a driver (not shown) for rotatably driving shaping member 304. Examples of suitable sources which can couple to coupler 305 for driving shaping member 304 include, for example, drills, hand crank, motors, or any other device which can rotate the shaping member 304.

In the illustrated embodiment, shaping member 304 comprises a shaping cylinder 310 having a shaping surface 311 configured to provide a particular shape to the bone. In the illustrated embodiment, two shaping surfaces 311 are present. A first shaping surface 312 includes a plurality of rows of raised cutting teeth 313 for cutting serrations into the bone when shaping cylinder 310 is rotated. A second shaping surface 314 includes a plurality of cutting teeth 315 positioned in a single plane which is perpendicular to the long axis of shaping cylinder 310. Second shaping surface 314 can be used for cutting a notch into either side of a piece of bone. Such a notch would, for example, permit gripping of the piece of bone on two sides when placing the shaped bone into a surgical site.

Figure 40:
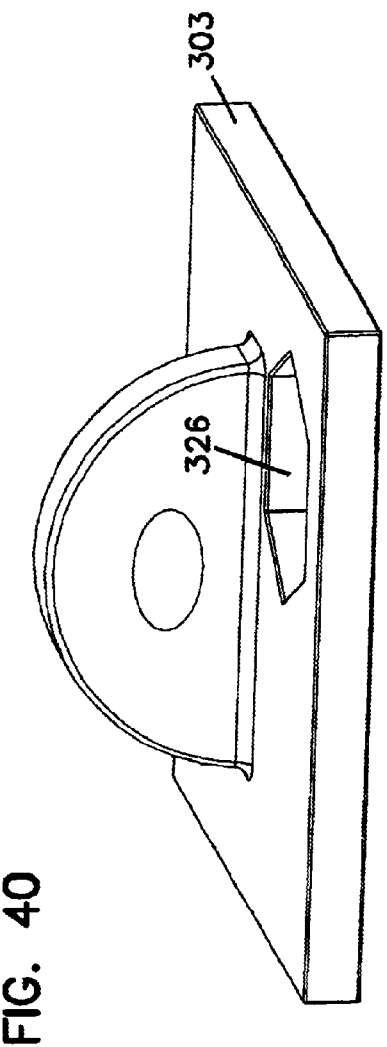
FIG. 40 is a perspective view of a cover guide of a shaping assembly according to the invention.

Table surface 302 provides a flat surface along which a piece of bone can be passed when shaping. Table surface 302 includes an aperture 320 through which the teeth 313, 315 protrude above table surface 302. Each of screws 322a–d have heads 323a–d, respectively. When screws 322a–d are passed through holes 324a–d, respectively, to secure table surface 302 to frame 301, heads 323a–d are configured to protrude an appropriate distance to maintain the bottom surface 325 of cover guide 303 above table surface 302. In one embodiment, the distance will be about the height that cutting teeth (or other shaping surface) protrude above table surface 302. Cover guide 303 provides for guiding a piece of bone along the table surface 302 and shaping surfaces 311 when in use. FIG. 40 illustrates cover guide 303 rotated 180° from the view in FIG. 39 illustrating an opening 326 for receiving a piece of bone to be shaped by the assembly 300.

Figure 41:
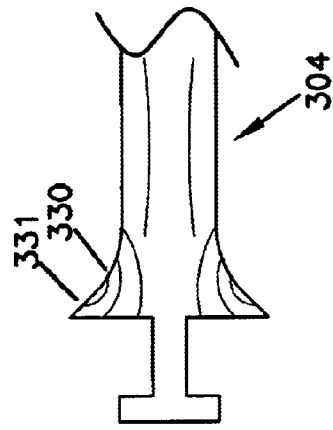
FIG. 41 is a view of a concave cutting surface for a shaping member according to the invention.

FIG. 41 is a profile view of an alternative embodiment of a shaping member 304 having a concave cutting surface 330 which includes, for example, cutting flutes 331 for forming a rounded edge on a piece of bone.

Figure 42:
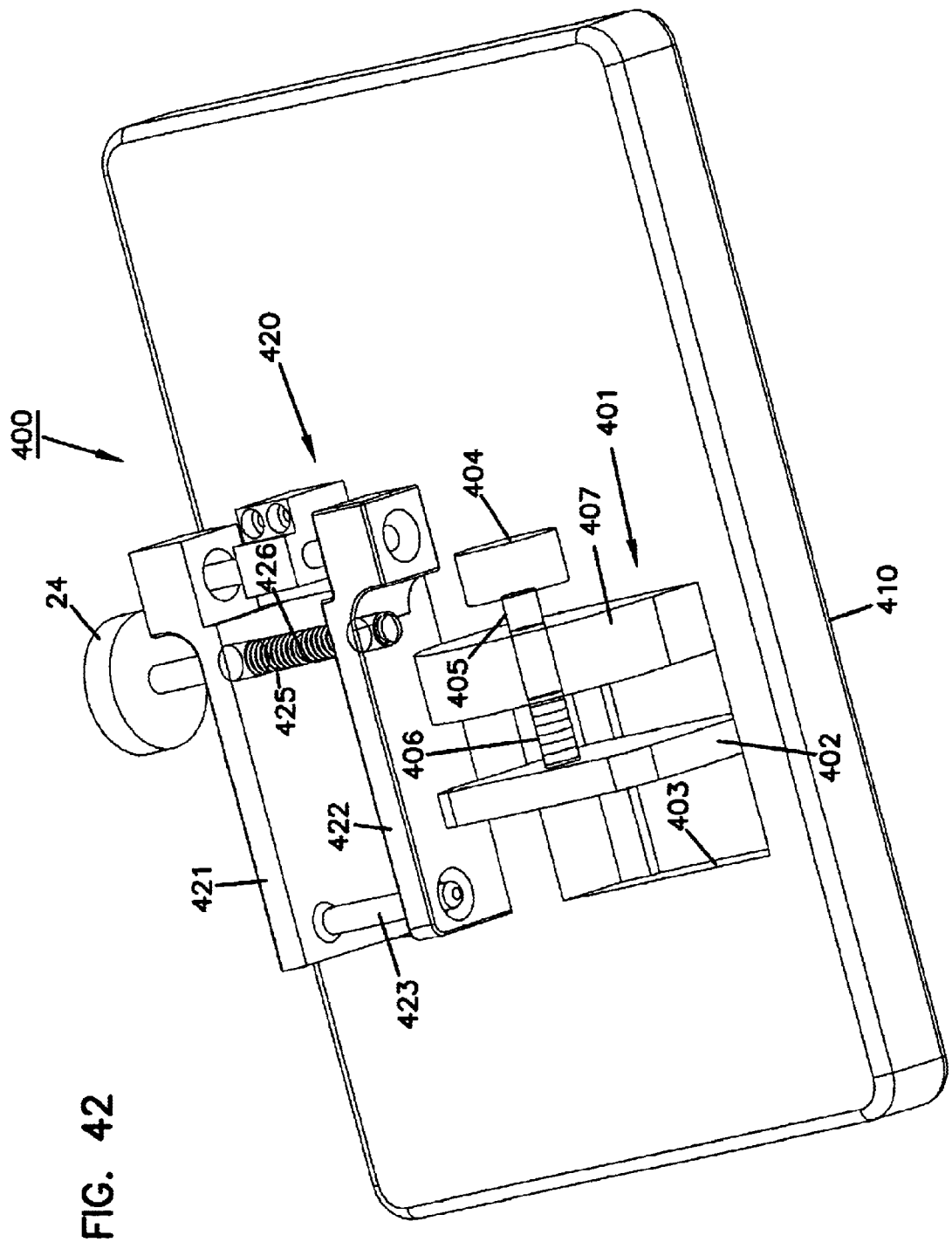
FIG. 42 is a perspective view of a bone holding arrangement according to the invention.
Figure 43:
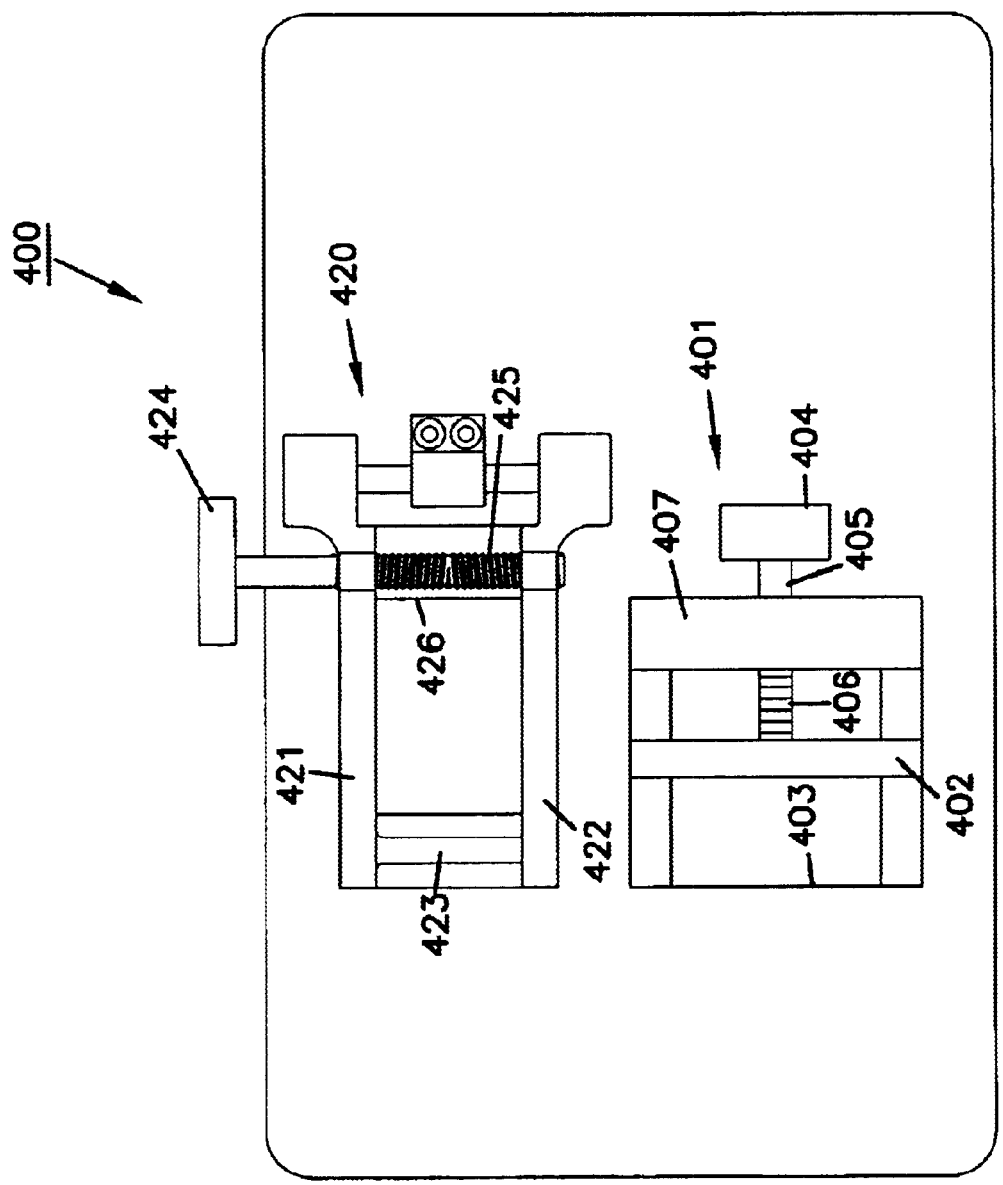
FIG. 43 is a top plan view of the bone holding arrangement of FIG. 42.

FIGS. 42 and 43 illustrate an embodiment bone holding assembly 400 according to the invention. In use, the bone holding assembly 400 can be used to safely hold a piece of bone when cutting serrations, grooves, rounding edges, or forming other shapes when using a bone shaping assembly such as that shown in FIG. 39. In the illustrated embodiment, bone holding assembly 400 includes two different bone vices for securing a piece of bone. In a first bone vice 401, a single mobile compression plate 402 can selectively apply a compression force to secure the piece of bone. Mobile compression plate 402 can be moved towards vertical edge 403 by rotating knob 404 mounted to threaded shaft 405. The male threads 406 on threaded shaft 405 cooperate with female threads (not visible) present in a bore (not visible) passing through shaft guide 407.

In use, once the bone is in place, the planar bottom surface 410 of bone holding assembly 400 can be slid along table surface 402 of bone shaping assembly 300 to pass the bone over one or both of rotating shaping surfaces 311 as needed.

Bone holding assembly 400 also includes a second bone vice 420. In this arrangement, two mobile compression plates 421, 422 are arranged such that when moved toward one another, the bone is fixed in position between the plates by compression force. In the illustrated embodiment, first mobile compression plate 421 and/or second bone compression plate 422 can freely move relative to one another along a threadless shaft 423 when knob 424 is rotated. Knob 425 is attached to counter-threaded shaft 425. The counter-thread configuration 426 is best appreciated in the top plan view of FIG. 43.

Once a piece of bone is in place in second bone vice 420, the bone holding arrangement can be slid along table surface 302 of bone shaping assembly 300 as described for first bone vice 401. It will be appreciated that one, two, or more bone vices can be present on a single bone holding arrangement.

From the foregoing detailed description, it will be evident that modifications and variations can be made in the devices and methods of the invention without departing from the spirit or scope of the invention. Therefore, it is intended that all modifications and variations not departing from the spirit of the invention come within the scope of the claims and their equivalents.

What is claimed is:

1. A bone jig comprising:
   a base;
   a bone holding arrangement; and
   a bone cutting arrangement including a first cutting block and a second cutting block, wherein the first and second cutting blocks are capable of pivoting relative to one another.

2. The bone jig according to claim 1 wherein the bone holding arrangement comprises a first and second bone holding member.

3. The bone jig according to claim 2 wherein the first bone holding member includes a first gripping end, the second holding member includes a second gripping end, the first and second gripping ends adapted to provide a four-point contact with a piece of bone when the bone is positioned in the holding arrangement.

4. The bone jig according to claim 2 wherein the first and second bone holding members each have a detachable gripping end.

5. The bone jig according to claim 1 wherein the first and second cutting blocks each have a slot for passing a saw blade therethrough.

6. The bone jig according to claim 1 further comprising a first pair of support arms and a second pair of support arms, the first pair of support arms capable of moving to and fro relative to the second pair of support arms.

7. The bone jig according to claim 6 wherein the second pair of support arms can move to and fro relative to the first pair of support arms.

8. A method for shaping bone comprising:
   selecting a piece of bone to be shaped;
   selecting a bone guide for shaping the bone, the bone guide comprising:
   (i) a base;
   (ii) a bone holding arrangement; and
   (iii) a bone cutting arrangement including a first and second cutting guides, wherein the first and second cutting guides are capable of pivoting relative to one another;
   positioning the bone in the bone holding arrangement; and
   shaping the bone with the bone guide.

* * * * *